United States Patent
Hong et al.

(10) Patent No.: US 10,990,168 B2
(45) Date of Patent: Apr. 27, 2021

(54) COMPENSATING FOR A MOVEMENT OF A SENSOR ATTACHED TO A BODY OF A USER

(71) Applicants: Injoon Hong, Plano, TX (US); Long Le, Richardson, TX (US); Sourabh Ravindran, Dallas, TX (US)

(72) Inventors: Injoon Hong, Plano, TX (US); Long Le, Richardson, TX (US); Sourabh Ravindran, Dallas, TX (US)

(73) Assignee: Samsung Electronics Co., Ltd., Suwon-si (KR)

( * ) Notice: Subject to any disclaimer, the term of this patent is extended or adjusted under 35 U.S.C. 154(b) by 98 days.

(21) Appl. No.: 16/214,462

(22) Filed: Dec. 10, 2018

(65) Prior Publication Data

US 2020/0183488 A1     Jun. 11, 2020

(51) Int. Cl.
    *G06F 3/01*          (2006.01)
    *G06K 9/00*       (2006.01)
    (Continued)

(52) U.S. Cl.
    CPC .............. *G06F 3/013* (2013.01); *A61B 3/113* (2013.01); *A61B 3/14* (2013.01); *A61B 5/0205* (2013.01); *A61B 5/6803* (2013.01); *A61B 5/721* (2013.01); *G01P 13/00* (2013.01); *G06F 3/012* (2013.01); *G06K 9/0061* (2013.01); *G06T 3/00* (2013.01); *A61B 5/0402* (2013.01);
    (Continued)

(58) Field of Classification Search
    CPC ......... G06F 3/013; G06F 3/012; A61B 3/113; A61B 3/14; A61B 5/0205; A61B 5/6803; A61B 5/721; A61B 5/0402; A61B 5/0476; A61B 5/0496; A61B 5/14542; A61B 5/4806; A61B 5/6823; A61B 5/6824; A61B 5/6828; A61B 5/6831; G01P 13/00; G06K 9/0061; G06T 3/00
See application file for complete search history.

(56) References Cited

U.S. PATENT DOCUMENTS 6,369,952 B1    4/2002   Rallison
8,587,659 B1   11/2013   Socolinsky
(Continued)

FOREIGN PATENT DOCUMENTS

KR           1576567         6/2011
KR         10-1857466        5/2018
KR      101857466 B1 *    5/2018

OTHER PUBLICATIONS

Written Opinion of the International Searching Authority and International Search Report, PCT/KR2019001685 published Sep. 9, 2019.
B. Pires et. al, "Visible-Spectrum Gaze Tracking for Sports", CVPR workshop 2013.

*Primary Examiner* — Brenda C Bernardi
(74) *Attorney, Agent, or Firm* — John J. King

(57) ABSTRACT

A method of compensating for a movement of a device worn by a user is described. The method comprises measuring, using a first sensor, a motion of a user wearing the device; measuring, using a second sensor, a motion of the device; determining a difference in the motion of the device with respect to the motion of the user; and compensating for the difference in the motion of the device with respect to the motion of the user. An electronic device for monitoring a device worn by a user is also disclosed.

20 Claims, 5 Drawing Sheets

(51) Int. Cl.
- *G06T 3/00* (2006.01)
- *A61B 5/0205* (2006.01)
- *A61B 5/00* (2006.01)
- *A61B 3/13* (2006.01)
- *A61B 3/14* (2006.01)
- *G01P 13/00* (2006.01)
- *A61B 5/0402* (2006.01)
- *A61B 5/0476* (2006.01)
- *A61B 5/0496* (2006.01)
- *A61B 5/145* (2006.01)
- *A61B 3/113* (2006.01)

(52) U.S. Cl.
CPC ........... *A61B 5/0476* (2013.01); *A61B 5/0496* (2013.01); *A61B 5/14542* (2013.01); *A61B 5/4806* (2013.01); *A61B 5/6823* (2013.01); *A61B 5/6824* (2013.01); *A61B 5/6828* (2013.01); *A61B 5/6831* (2013.01)

(56) References Cited

U.S. PATENT DOCUMENTS

| | | | |
|---|---|---|---|
| 9,788,714 B2 | 10/2017 | Krueger | |
| 2014/0160170 A1* | 6/2014 | Lyons | G09G 5/38 |
| | | | 345/676 |
| 2015/0070274 A1 | 3/2015 | Morozov | |
| 2017/0124928 A1 | 5/2017 | Edwin et al. | |
| 2017/0172675 A1 | 6/2017 | Jarc et al. | |
| 2017/0180720 A1 | 6/2017 | Jarc et al. | |
| 2017/0357333 A1 | 12/2017 | Balan | |
| 2017/0357334 A1 | 12/2017 | Balan | |
| 2018/0032103 A1 | 2/2018 | Eskilsson | |
| 2018/0084232 A1 | 3/2018 | Belenkii | |
| 2018/0144483 A1 | 5/2018 | Kang et al. | |
| 2018/0357978 A1* | 12/2018 | Liao | A63F 13/30 |
| 2019/0192053 A1* | 6/2019 | Saigh | G16H 20/30 |
| 2020/0035203 A1* | 1/2020 | Kosik | G06F 3/015 |

* cited by examiner

Timing Diagram of High-Speed ET with IMU

COMPENSATING FOR A MOVEMENT OF A SENSOR ATTACHED TO A BODY OF A USER

FIELD OF THE INVENTION

An embodiment of the invention relates generally to wearable devices that capture data, and in particular, to a method of compensating for a movement of a sensor attached to a body of a user.

BACKGROUND OF THE INVENTION

Sensors are often used in electronic devices to detect information. For example, eye tracking (ET) technology can be used to provide an estimate of a user's point of gaze on 2D display screen or for identifying objects in a real-world environment. The use of eye tracking has particular application for eyewear, such as glasses or headsets that may be used in augmented reality (AR) and virtual reality (VR). Generally, ET uses a gaze-mapping function which maps a pupil-center point in eye camera coordinate into a gaze-point in the target system coordinate.

However, it is difficult to obtain high accuracy of ET because the eyewear may slip on a user's nose. Since the mapping function implicitly contains a geometrical relationship between two coordinate systems, if the eyewear slips on user's nose, the previous mapping function with the old geometry information will map to erroneous gaze-points in the target coordinate system. A slip of the eyewear may cause the user's calibration function to be corrupted, requiring the user to conduct another calibration process. Because the calibration function is sensitive to eyewear movement, even a small amount of slip could generate large errors in gaze estimation. Such a calibration process for obtaining the new mapping function using conventional devices may take an unacceptable amount of time, such as approximately 30 seconds.

In order to solve problems associated with the slipping of eyewear, conventional devices use a vision-based approach that estimates the eyewear movement by tracking features points of eyes, such as eye corners. However, vision-based slip compensation is not robust, and can fail due to occlusion, blurriness, etc. Further, such a vision-based approach cannot estimate full 6 degree of freedom movement information without complex triangulation or simultaneous location and mapping (SLAM) techniques, which may require significant computational resources. Any assumption that a sensor such as eyewear can move only in certain direction to reduce the amount of computational resources may eventually degrade accuracy of the slip compensation.

Accordingly, there is a need for a method for compensating for the movement of a sensor worn on the body of a user.

SUMMARY OF THE INVENTION

A method of compensating for a movement of a device worn by a user is described. The method comprises measuring, using a first sensor, a motion of a user wearing the device; measuring, using a second sensor, a motion of the device; determining a difference in the motion of the device with respect to the motion of the user; and compensating for the difference in the motion of the device with respect to the motion of the user.

An electronic monitoring system for monitoring a device worn by a user is also described. The electronic monitoring system comprises a processor coupled to receive data from a first sensor, wherein the processor measures, using a first sensor, a motion of a user wearing the device; measures, using a second sensor, a motion of the device; determines a difference in the motion of the device with respect to the motion of the user; and compensates for the difference in the motion of the device with respect to the motion of the user.

A non-transitory computer-readable storage medium having data stored therein representing instructions executable by a processor performs a method comprising measuring, using a first sensor of a device, a motion of the device; measuring, using a second sensor, a motion of the device; determining a difference in the motion of the device with respect to the motion of the user; and compensating for the difference in the motion of the device with respect to the motion of the user.

DETAILED DESCRIPTION OF THE DRAWINGS

The circuits and methods set forth below enable the detection of slip of a sensor, such as a sensor worn on a body, to compensate for the slip of the sensor. According to some implementations, the slip of eyewear used in AR and VR applications can be detected. To overcome accuracy and speed limitations of the conventional approaches to compensate for a slip or other movement of a sensor worn by a user, a sensor-based compensation method is described.

According to one implementation, a sensor, such as an inertial measurement unit (IMU), has the accuracy to provides full 6 degree-of-freedom information after some post-processing on raw-data of the IMU. The use of an IMU sensor to estimate the 6 degree-of-freedom information also does not require complex vision algorithms, such as triangulation or SLAM. In addition, an IMU is a very high-speed component which could generate data more quickly than a camera, such as rate greater than 200 Hz. Since the IMU sensor is generally faster than a camera image sensor, IMU-based slip compensation for the slip of a sensor is faster than the vision-based compensation method.

According to another implementation, a temple-glass differential IMU sensor configuration comprises temple-mounted and glass-mounted IMU sensors of eyewear, where head movements are canceled to enable measuring the glass-to-head transformation representing a slip of the eyewear. IMU-based slip estimation does not suffer from vision-based drawbacks (e.g. occlusion, blurriness, up-to-scale, etc.), provides accurate estimates since slip is small in translation, provides low-latency estimates, and low power consumption.

While the specification includes claims defining the features of one or more implementations of the invention that are regarded as novel, it is believed that the circuits and methods will be better understood from a consideration of the description in conjunction with the drawings. While various circuits and methods are disclosed, it is to be understood that the circuits and methods are merely exemplary of the inventive arrangements, which can be embodied in various forms. Therefore, specific structural and functional details disclosed within this specification are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting, but rather to provide an understandable description of the circuits and methods. It should be understood that the phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, or A and B and C.

Figure 1:
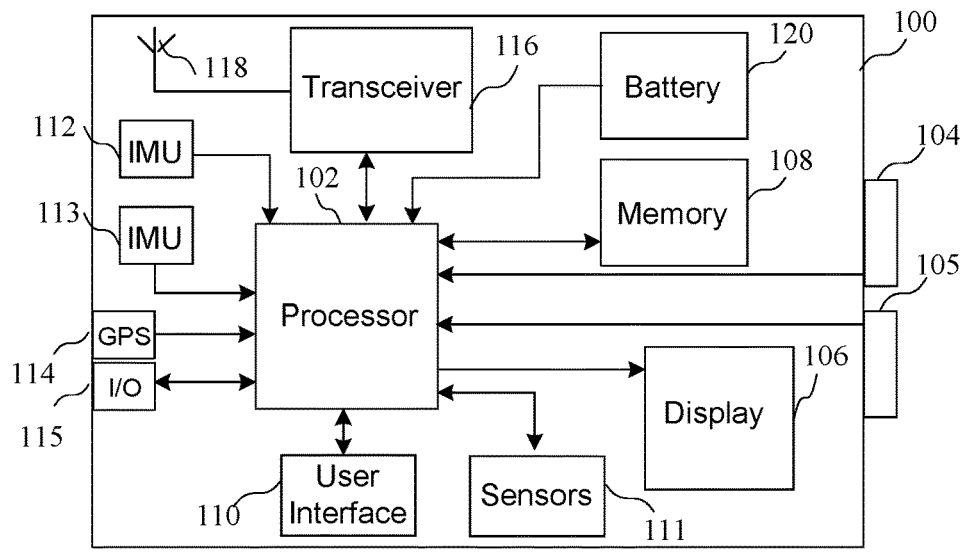
FIG. 1 is an exemplary block diagram of an electronic device which may be wearable.

Turning first to FIG. 1, an exemplary block diagram of an electronic device which may be wearable is shown. The exemplary electronic device 100 that may be any type of device having one or more cameras. The mobile device 100 may comprise a processor 102 coupled to a plurality of cameras 104 and 105. The mobile device 100 could be any type of device adapted to transmit and receive information, such as a smart phone, tablet or other electronic device receiving or providing information, such as a wearable device. The processor 102 could be an ARM processor, an X86 processor, a MIPS processor, a graphics processing unit (GPU), a general purpose GPU, or any other processor configured to execute instructions stored in a memory. The processor 102 could be implemented in one or more processing devices, where the processors may be different. For example, the electronic device could include a central processing unit (CPU) as well as a GPU for example. The operation of the processing circuit may rely upon both software and hardware to implement various features of the circuits and methods set forth below.

The processor 102 may be coupled to a display 106 for displaying information to a user. The processor 102 may also be coupled to a memory 108 that enables storing information related to data or information associated with image data. The memory 108 could be implemented as a part of the processor 102, or could be implemented in addition to any cache memory of the processor, as is well known. The memory 108 could include any type of memory, such as a solid state drive (SSD), Flash memory, Read Only Memory (ROM) or any other memory element that provides long term memory, where the memory could be any type of internal memory of the electronic drive or external memory accessible by the electronic device.

A user interface 110 is also provided to enable a user to both input data and receive data. Some aspects of recording images may require user's manual input. The user interface 110 could include a touch screen user interface commonly used on a portable communication device, such as a smart phone, smart watch or tablet computer, and other input/output (I/O) elements, such as a speaker and a microphone. The user interface 110 could also comprise devices for inputting or outputting data that could be attached to the mobile device by way of an electrical connector, or by way of a wireless connection, such as a Bluetooth or a Near Field Communication (NFC) connection.

The processor 102 may also be coupled to other elements that receive input data or provide data, including various sensors 120, an inertial measurement unit (IMU) 112 and a Global Positioning System (GPS) device 114 for activity tracking. For example, first inertial measurement unit (IMU) 112 can provide various information related to the motion or orientation of the device, while a second IMU 113 can be used to other information association with motion of the device, which can be used to find slip of a sensor, as will be described in more detail below. A GPS 114 provides location information associated with the device.

Other sensors, which may be a part of or coupled to a mobile device, may include by way of example a light intensity (e.g. ambient light or UV light) sensor, a proximity sensor, an environmental temperature sensor, a humidity sensor, a heart rate detection sensor, a galvanic skin response sensor, a skin temperature sensor, a barometer, a speedometer, an altimeter, a magnetometer, a hall sensor, a gyroscope, WiFi transceiver, or any other sensor that may provide information related to detecting a state or condition on the body or will be described in more detail below. The processor 102 may receive input data by way of an input/output (I/O) port 115 or a transceiver 116 coupled to an antenna 118. While the elements of the electronic device are shown by way of example, it should be understood that other elements could be implemented in the electronic device of FIG. 1, or electronic devices that are arranged differently to implement the methods set forth below.

Figure 2:
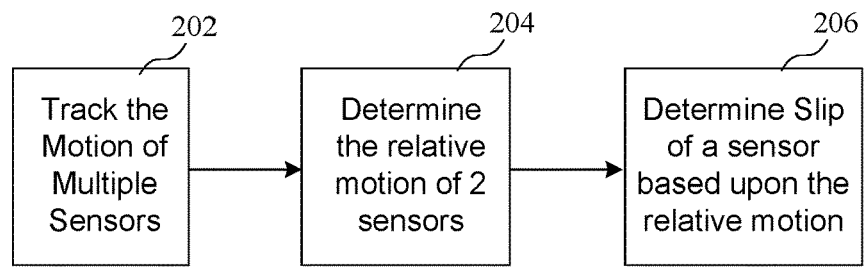
FIG. 2 is an exemplary diagram showing a process of measuring the slip of a sensor.

Turning now to FIG. 2, an exemplary diagram shows a process of measuring the slip of a sensor. The motion of multiple sensors is tracked at a block 202. The multiple sensors could be implemented on a single electronic device, such as a piece of eyewear for example. Alternatively, the multiple sensors could be distributed. For example, for an implementation of a method of determining a slip of a sensor associated with eyewear, one of the sensors may be implemented on the eyewear, and the other sensor may be implemented on the portion of the body of the user wearing the eyewear, such as the head. The motion of the multiple sensors may be used with other devices, including any type of device worn on the body, where the motion of one sensor can be determined with respect to another sensor. The relative motion of two of the sensors is determined at a block 204, and the slip of a sensor is then determined based upon the relative motion of the one sensor with respect to the other sensor at a block 206. According to one implementation, the motion of eyewear can be monitored by at least 2 sensors to determine what component of the motion is associated with motion of the head, where another component of the motion would be associated with a slip of the eyewear. While eyewear is used by way of example, the relative motion of 2 sensors can be used to determine slip of one of the sensors attached to the body of a user.

Figure 3:
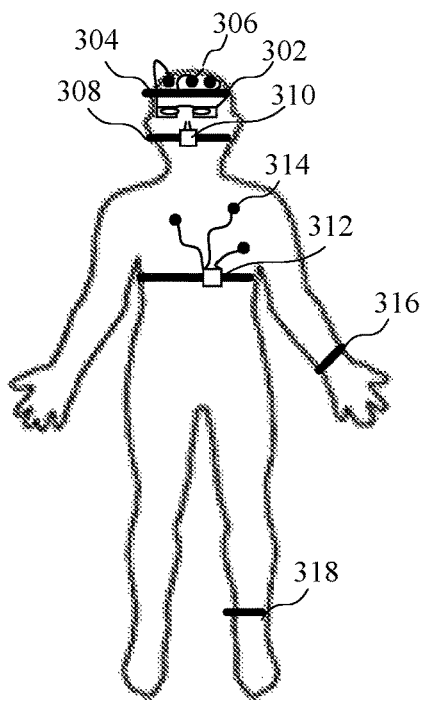
FIG. 3 is an exemplary diagram a user having a variety of wearable sensors.

Turning now to FIG. 3, an exemplary diagram a user having a variety of wearable sensors is shown. As shown in FIG. 3, a variety of sensors can be worn by a user, where the relative motion of two sensors can be used to detect a slip of one of the sensors. In addition to eyewear having one or more sensors as will be described in more detail below, other sensors worn on the body may include for example a headband 304 having a sensor 306, which may be an electroencephalogram (EEG) monitor, a face mask 306 which may comprise a sensor 310 for detecting one or more aspects of breathing, including sensors to monitor the respiration process and the chemical content of exhaled air (e.g. oxygen and carbon dioxide levels in the blood), a chest band 321 having sensors 314 for an electrocardiogram (EKG) measurement, a wrist band 316 for determining pulse or the movement of the hand and/or arm, and an ankle band 318 for detecting a movement of the leg. The mask may further comprise sensor for generating a recording chin and eye movements, and the resting potential of the retina (i.e. an electrooculogram).

According to one implementation, these sensors may be mounted on a patient by a technician for a sleep study for example, and can slip during the sleep study (where a patient goes to sleep, and hence exhibits uncontrolled forces on the sensors), causing the measurements to be incorrect and prompt responses from a technician. The data from sensors on the body that have slipped may be incorrect data. Detecting a sensor that has slipped as described above in reference to FIG. 2 can reduce or eliminate incorrect data readings. While specific sensors are shown by way of example in FIG. 3, it should be understood that other sensors could be used.

Figure 4:
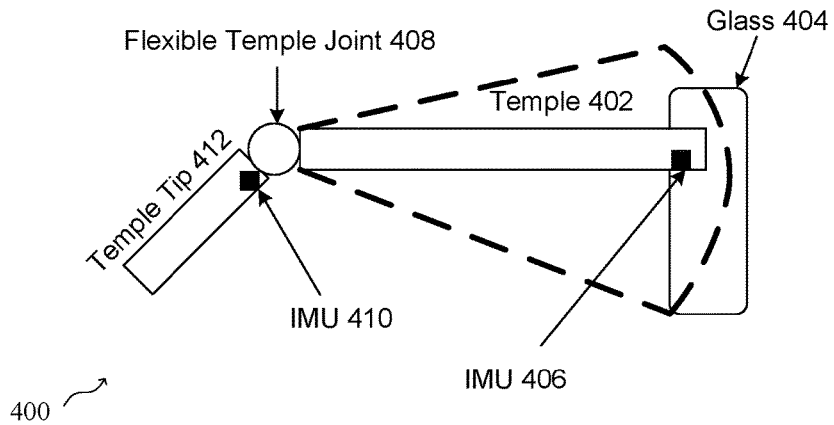
FIG. 4 is an exemplary block diagram showing a possible slip of eyewear when worn by a user.

Turning now to FIG. 4, an exemplary block diagram shows a possible slip of eyewear when worn by a user. According to the implementation of FIG. 4, eyewear 400 comprises 2 sensors, one sensor that is used for the detection of the motion of the head and another sensor that is used for detecting movement of the eyewear (i.e. on the head), where the difference would represent the slip of the glasses. More particularly, temple portions 402 of the eyewear extend from a glass portion 404, which may be a display of an HMD or a lens of smart glasses for example. A first IMU 406 may be provided near the glass portion. The IMU 406 is implemented to detect slip of the eyewear, as shown for example along the dashed line arc located between the two dashed lines extending from the temple. That is, any slip of the eyewear would generally be detected based upon movement of the glass portion along the dashed line arc. A second IMU 410 is used to detect a motion of the head, and may be located on the eyewear. As shown in FIG. 4, IMU 410 is placed on the temple tip 412. The relative motion of the head could be detected by the IMU 410, and used to determine the component of the motion detected by the IMU 406 that is attributed to a slip of the eyewear (i.e. the motion of the glass 404). That is, by placing the IMU 410 on the temple tip 412, the IMU 410 would not be affected by the slip of the eyewear, and the motion detected by the IMU 410 would be primarily attributed to the motion of the head.

While the IMU 410 is shown by way of example on the eyewear 400, it should be understood that the IMU 410 could be separate from the eyewear, but would otherwise detect the motion of the head. That is, the IMU 410 captures head motion, while the IMU 406 captures both head motion and eyewear slip with respect to the head, and the difference between measurements can be used to determine the eyewear slip. It should be understood that eyewear can include any type of device that is placed in front of the eye, which may have at least one of a screen and a lens, including devices that are worn on the head, such as smart glasses (e.g. a Google Glass device) or head mounted devices (HMDs) used in AR or VR.

Figure 5:
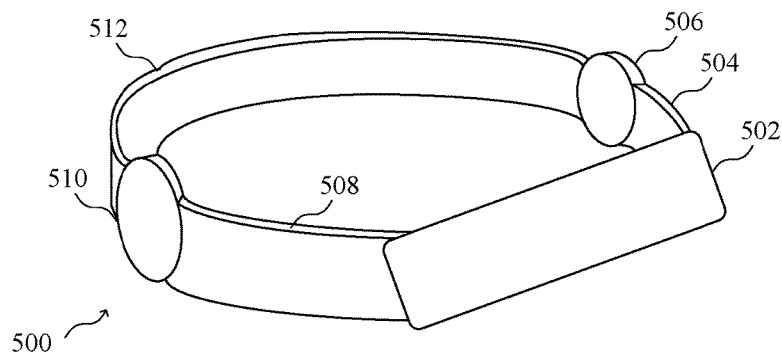
FIG. 5 shows another example of eyewear worn by a user having a head band.

Turning now to FIG. 5, another example of eyewear 500 worn by a user and having a head band is shown. According to the example of FIG. 4, a glass portion 502 is coupled to a first temple portion 504 having a first flexible temple joint 506. The glass portion 502 is also coupled to a second temple portion 508 having a second flexible temple joint 510. A head band 512, which may be positioned on the back of the head for example, extends between the first flexible temple joint 506 and the second flexible temple joint 510 to secure the eyewear to the head of a user. The eyewear 500 of FIG. 5 can include IMUs, such as an IMU associated with the temple to detect slip of the glass 502 and an IMU associated with another portion of the eyewear 500, such as the head band 512. As described above in reference to FIG. 4, the IMU associated with the head band may capture head motion, while the IMU associated with the glass may capture both head motion and eyewear slip with respect to the head, where the difference between measurements can be used to determine the eyewear slip.

Figure 6:
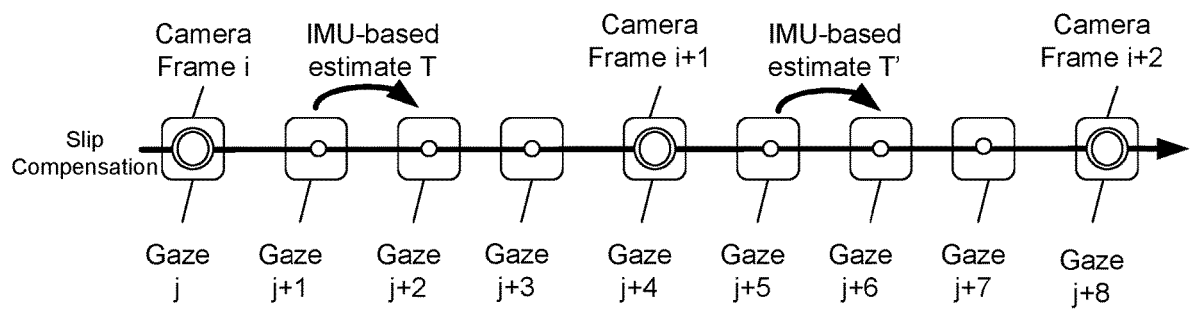
FIG. 6 is a diagram showing IMU rate with respect to a camera frame rate.

Turning now to FIG. 6, a diagram shows IMU rate for capturing data with respect to a camera frame rate. Unlike implementations where there is no compensation for a slip between camera frames (when using a conventional technique that relies upon images captured by the camera), an implementation relying upon data from sensors, such as IMU data, enables corrections to compensate for slip between camera frames, as shown in FIG. 6. Because the response rate of the IMU is faster than the frame rate of the camera, compensation for a slip of the eyewear can be made faster. That is, data from sensors can be generated at a faster rate then the camera frame rate, and therefore enable compensation for slip of eyewear faster than if compensation relied upon image data, which is generated more slowly. In other words, IMU-based approach enables low-latency slip compensation, i.e. the slip compensation is done with a minimal latency after a slip happens. According to some implementations, IMU provides 6-degrees of freedom (6-dof) and 3D movement information at a rate of approximately 200 Hz, compared to a conventional camera speed of approximately 60 Hz or 120 Hz. The use of sensor data such as IMU data enables compensation for a slip of the eyewear without a complex algorithm such as SLAM, which may be required when using camera data.

Figure 7:
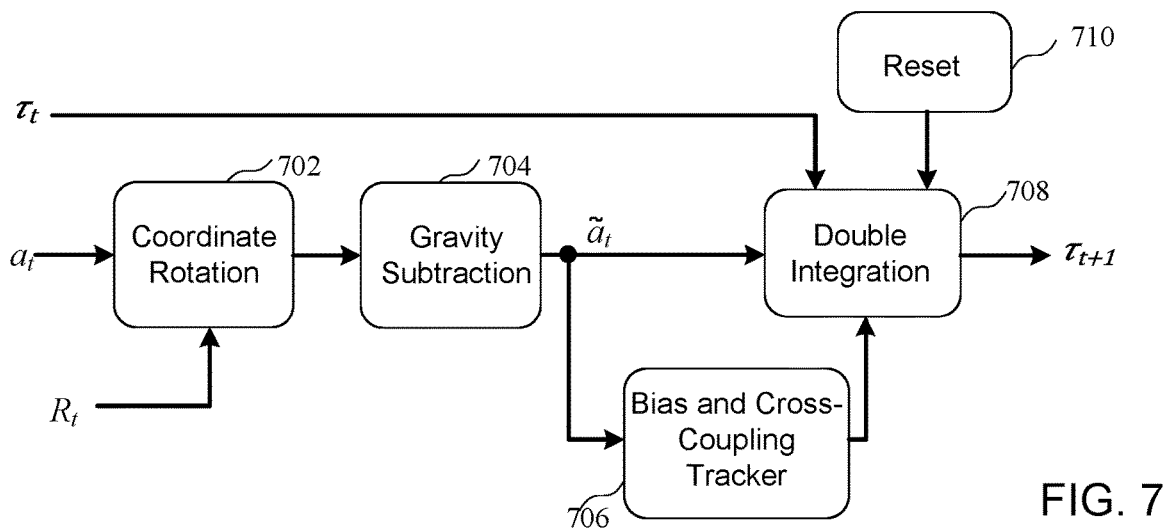
FIG. 7 is a block diagram showing the generation of an IMU translation estimation.

Turning now to FIG. 7, a block diagram shows the generation of an IMU translation estimation. As shown in FIG. 7, a coordinate rotation block 702 is adapted to receive acceleration data ($a_r$), which may be provided from an IMU, and a current rotation $R_r$, which may be provided from the orientation estimation in FIG. 8. Because the IMU is exposed to gravity, a gravity subtraction block 704 subtracts a gravity component to generate a linear acceleration value $ã_r$. Coordinate rotation and gravity subtraction convert raw accelerometer data into a linear acceleration value with the help of IMU-based orientation. The linear acceleration value is provided to both a bias and cross-coupling tracker block 606 and an integration block 708, where an output of the bias and cross-coupling tracker block 706 is also provided to the double integration block 708.

The bias and cross-coupling tracker block 706 may remove undesirable bias in the linear acceleration signal, and provide 3 degrees of freedom associated with the linear acceleration value to take into account motion in different directions. The bias and cross-coupling tracker block 706 enables 1) removing biases in each direction/axis, and 2)

compensating for motion leakage across directions, i.e. a portion of the motion in Y (e.g. vertical slip of the eyewear along the nose) is observed in X (e.g. horizontal axis of the eyewear) due to the IMU/sensor imperfection. That is, before integrating to obtain translation, bias and cross-coupling must be estimated and removed to mitigate error/drift in IMU-based translation estimation. By providing independent processing for each axis, improved bias and cross-coupling tracking can be performed, and therefore pose accuracy can be improved. Further, computationally expensive operations such as matrix inversion can be avoided later and therefore reduce pose latency.

According to one implementation, the bias and cross-coupling tracker block 706 and double integration block 708 are jointly specified by the following equations. For each axis, the cross-coupling terms of the other 2 axis in 3D space $m_1$ and $m_2$ are modeled as Brownian motion in block 706 as follows $$m_1 = m_1 + w_{m_1}; \text{ and} \qquad \text{Eq. 1}$$

$$m_2 = m_2 + w_{m_2} \qquad \text{Eq. 2}$$

where $w_{m_1}$ and $w_{m_2}$ are the corresponding noise terms. Herein, the = notation denotes the assignment operator since the estimation process is an iterative one.

The acceleration estimate a can be calculated as:

$$a_b = P_{a_b} \cdot a_b + (1 - P_{a_b}) \cdot a_i + w_{a_b}; \qquad \text{Eq. 3}$$

$$a_i = P_{a_i} \cdot a_i + (1 - P_{a_i}) \cdot \tilde{a}_i; \text{ and} \qquad \text{Eq. 4}$$

$$a = (a_i - a_b) + (a_{i,1} - a_{b,1}) \cdot m_1 + (a_{i,2} - a_{b,2}) \cdot m_2, \qquad \text{Eq. 5}$$

where $a_b$, $a_{b,1}$, $a_{b,2}$ represent the acceleration bias of the current and 2 other axes in 3D, respectively. $a_1$, $a_{i,1}$, $a_{i,2}$ represent the nominal acceleration of the current and 2 other axes in 3D, respectively. $\tilde{a}_t$ represents gravity-free/linear acceleration. Probabilistic weighting values (e.g. $Pa_b$ and $Pa_i$) can be used to provide data-driven tuning to reduce noise in the estimates of biases and intermediate values, and thus improve pose accuracy.

Velocity estimate v can also be calculated as:

$$v_b = P_{v_b} \cdot v_b + (1 - P_{v_b}) \cdot v_i + w_{v_b}; \qquad \text{Eq. 6}$$

$$v_i = v_i + a \cdot dt; \text{ and} \qquad \text{Eq. 7}$$

$$v = v_i - v_b \qquad \text{Eq. 8}$$

where $v_b$ represents velocity bias, $v_i$ represents nominal acceleration and v represents velocity estimate. Probabilistic weighting values (e.g. $Pv_i$) can also be used to reduce noise from the sensor. Finally, the drift-mitigated translation estimate is given by:

$$\tau_{t+1} = \tau_t + v \cdot dt \qquad \text{Eq. 9}$$

where τ represents translation.

A reset block 710 may be used to periodically reset the operation of generating the next translation $\tau_{t+1}$. That is, because the accumulated translation eventually drifts, it needs to be reset periodically at an appropriate rate. The same calculations are performed for data generated by both IMUs (e.g. IMUs 406 and 410), where the slip is taken as the difference between the motions observed by the glass-mounted IMU and temple-mounted IMU after it is transformed to the glass location.

Figure 8:
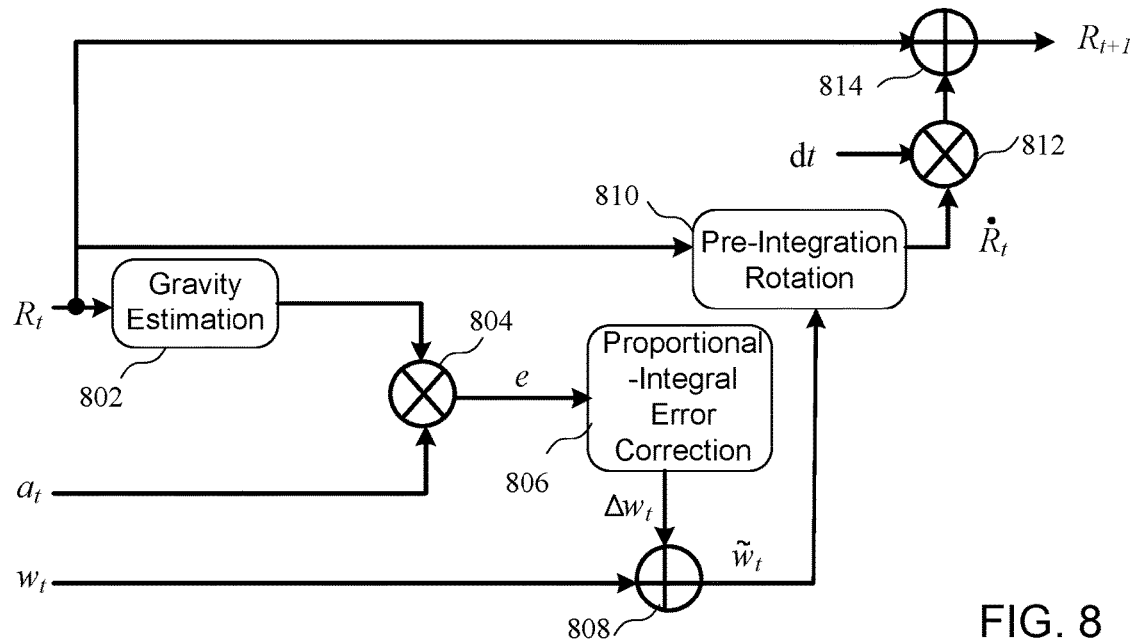
FIG. 8 is a block diagram showing the generation of an IMU orientation estimation.

Turning now to FIG. 8, a block diagram shows the generation of an IMU orientation estimation. More particularly, a gravity estimation block 802 is configured to receive the current rotation estimate $R_t$, and generate an output of which is coupled to a multiplier 804 that is also adapted to receive acceleration data at. The multiplier 804 generates error data e. The error data is provided to a proportional-integral error correction block 806, which generates a value that represents a correction value for gyroscope $\Delta w_t$. The gyroscope data $w_t$ is then added by an adder 808 to the correction for gyroscope $\Delta w_t$ to generate the corrected gyroscope data $\tilde{w}_t$. A pre-integration rotation block 810 is coupled to receive the corrected gyroscope data and current rotation data $R_t$ to generate the derivative $\dot{R}_t$ of $R_t$. A next rotation estimate is generated by multiplying the derivative $\dot{R}_t$ with the time step dt and added to the current rotation $R_t$ via the adder 814. The IMU orientation estimation can be performed by both of the IMUs (e.g. IMU 406 and 410), where the slip is taken as the difference between the motions observed by the glass-mounted IMU and temple-mounted IMU after it is transformed to the glass location. It should be noted that the circuits of FIGS. 7 and 8 could be implemented in hardware elements of the device, software elements, or using a combination of hardware and software, including the processor 102 and other elements of FIG. 1.

Figure 9:
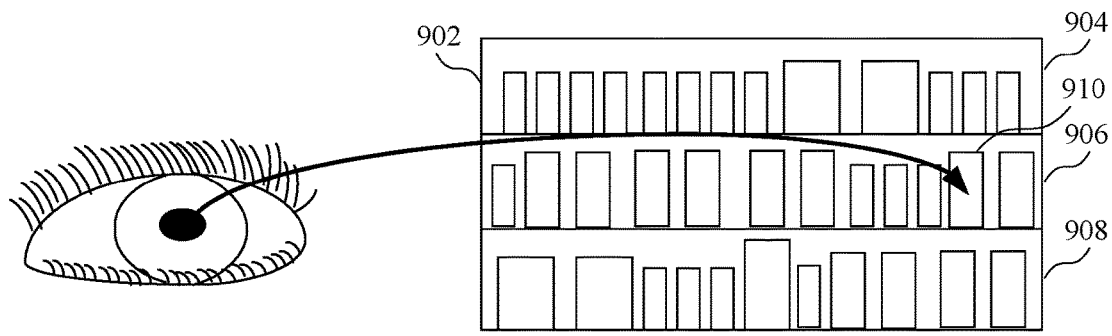
FIG. 9 is an image of an eye showing eye corner points.

Turning now to FIG. 9, an image of an eye showing eye corner points is shown. As shown in FIG. 9, the eye pupil enables defining an ellipse shape of the eye, which is generally defined as the portion of the eye exposed by the eyelids and is used as described in more detail below to implement a slip compensation method. Generally, an eye camera slip transform T=(τ, R), where τ and R are translation and orientation respectively, can be performed. An inverse transform $T^{-1}$ is performed on the slipped image. The gaze mapping is then performed after the transformation using a calibrated mapping function f, such as from the pupil-point in the transformed image to a gaze point on the display for example. More particularly, a display 902 show a portion of a shelves having items that may be of interest, including for example shelves 904, 906 and 908. As shown in FIG. 9, it can be determined that the eye is gazing at a gaze point corresponding to an item 910. Without slip compensation, a small pixel error in the pupil point can lead to a large pixel error in the gaze point.

Figure 10:
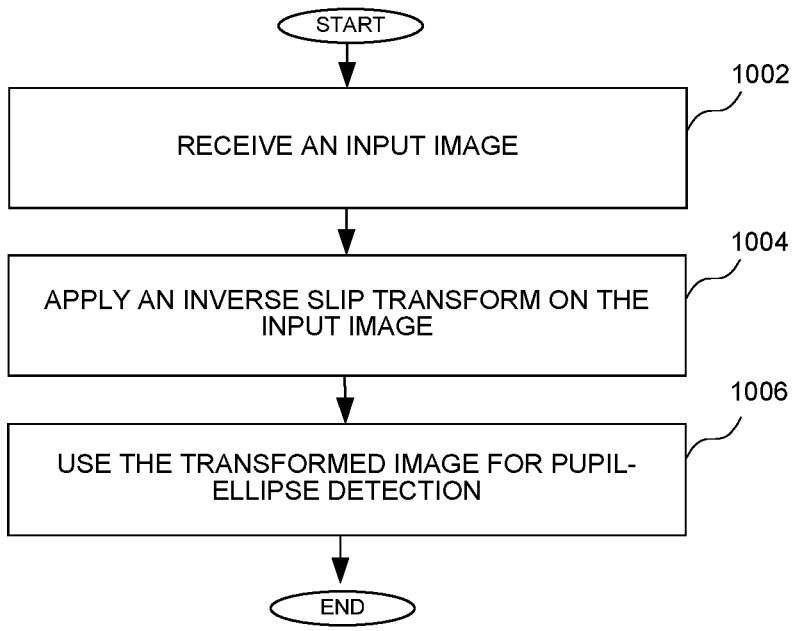
FIG. 10 is a flow diagram showing a direct slip compensation method.

According to one implementation, a direct slip compensation method can be implemented as shown in the flow diagram of FIG. 10. For example, a pupil and ellipse can be determined after applying an inverse transform slip on an input image. More particularly, an input image is received at a block 1002. An inverse slip transform applied on the input image at a block 1004. The transformed image is then used for pupil-ellipse detection at a block 1006 to enable compensating for the slip of the glasses.

Figure 11:
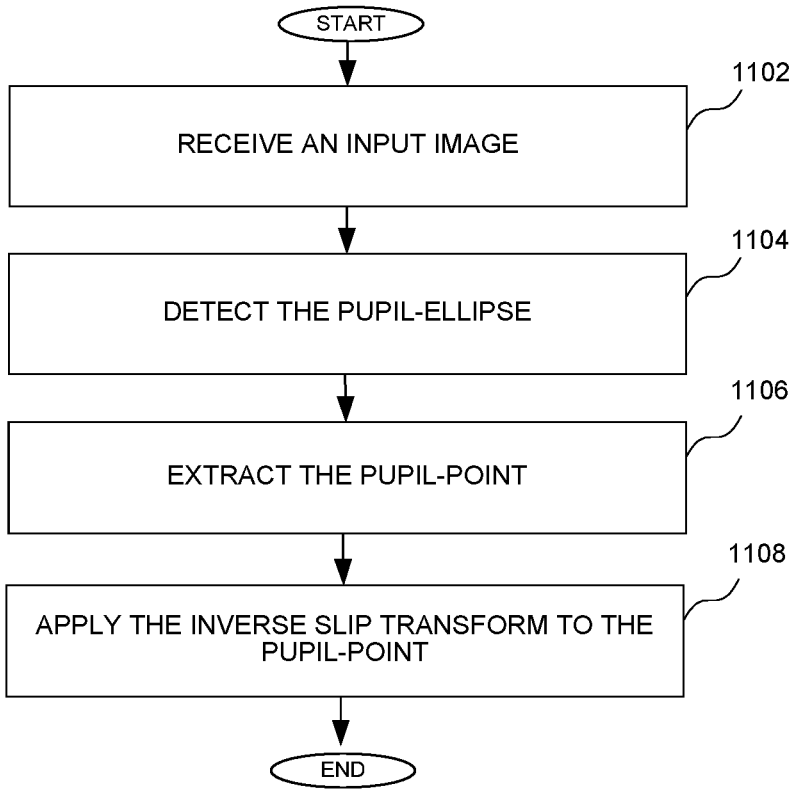
FIG. 11 is a flow diagram showing a point-transform slip compensation method.

Turning now to FIG. 11, a flow diagram shows a point-transform slip compensation method. According to the implementation of FIG. 11, the slip compensation can be based upon a pupil point (i.e. a center of a pupil). More particularly, an input image is received at a block 1102. The pupil-ellipse is detected at a block 1104. The pupil-point is extracted at a block 1106, and the inverse slip transform is applied to the pupil-point at a block 1108 to enable compensating for the slip of the glasses.

Figure 12:
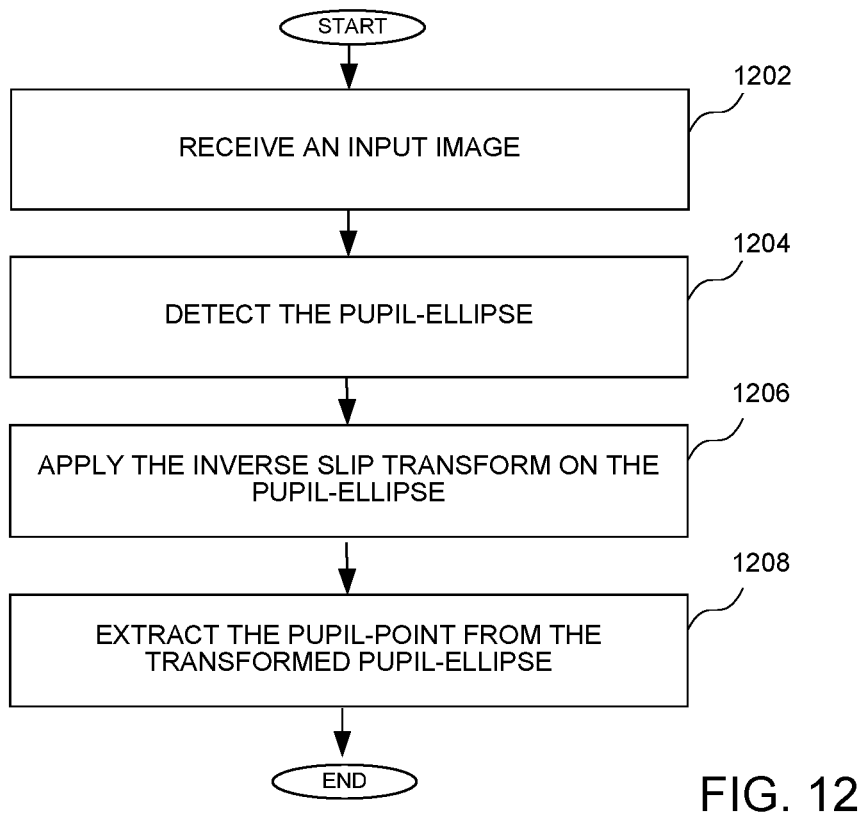
FIG. 12 is a flow diagram showing an ellipse-transform slip compensation method.

Turning now to FIG. 12, a flow diagram shows an ellipse-transform slip compensation method. An input image is received at a block 1202. According to the implementation of FIG. 12, the ellipse is used to identify a pupil point. More particularly, the pupil-ellipse is detected at a block 1204. The inverse slip transform applied on the pupil-ellipse at a block 1206. The pupil-point is extracted from the transformed ellipse at a block 1208 to enable compensating for the slip of the glasses.

Figure 13:
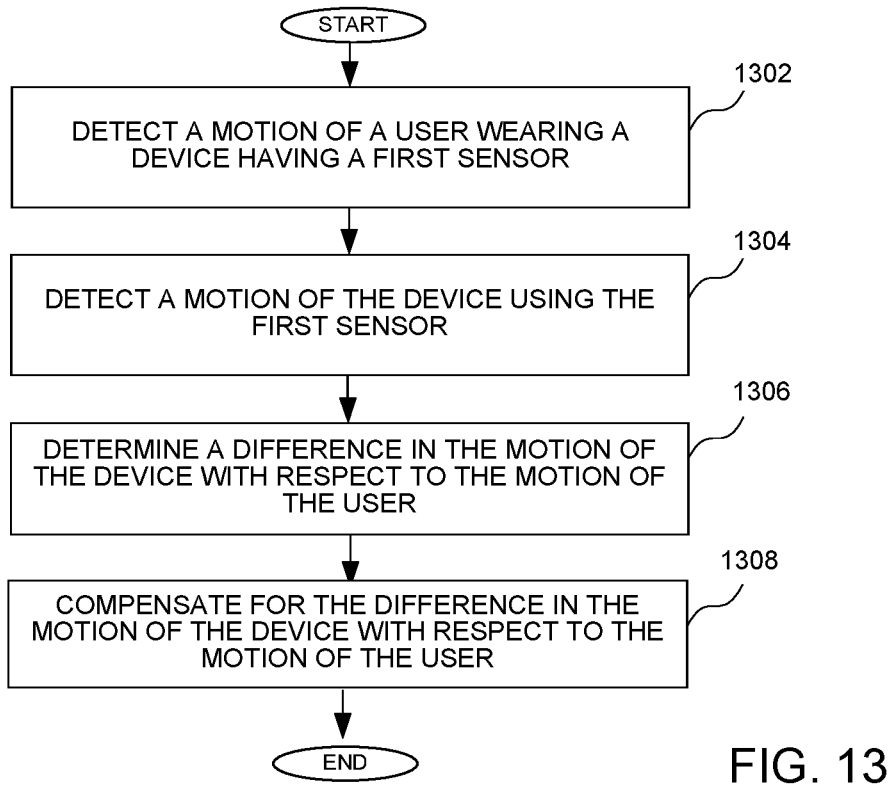
FIG. 13 is a flow diagram showing a method of compensating for a movement of a sensor attached to a body of a user.

Turning now to FIG. 13 is a flow diagram shows a method of compensating for a movement of a sensor attached to a body of a user. A motion of a user wearing a device having a first sensor detecting at a block 1302. The first sensor could be a sensor on eyewear, or any other sensor for detecting a state or condition of the body, as described above. A motion of the device using a second sensor is detected at a block 1304. For example, the second sensor could be another sensor associated with eyewear. A difference in the motion of the device with respect to the motion of the user is determined at a block 1306. For example, the difference in the motion of the device (e.g. the motion of eyewear on a head) and the motion of the head can be used to slip of the eyewear as described above. The difference in the motion of the device with respect to the motion of the user is compensated for at a block 1308. For example, the compensation can be used in any application requiring eye tracking, such as AR or VR.

According to some implementations, foveated rending can be used, where AR and VR headsets can reduce rendering workload by showing low resolution in peripheral vision areas. Because photoreceptors of the human eye are densely located in "fovea," and sparely located on the other side, there is no perceived resolution degradation with foveated rendering.

The various elements of the methods of FIGS. 10-13 may be implemented using the circuits of FIGS. 1-9 as described, or using some other suitable circuits. While specific elements of the method are described, it should be understood that additional elements of the method, or additional details related to the elements, could be implemented according to the disclosure of FIGS. 1-9.

It can therefore be appreciated that new circuits for and methods of compensating for movement of a sensor attached to a body have been described. It will be appreciated by those skilled in the art that numerous alternatives and equivalents will be seen to exist that incorporate the disclosed invention. As a result, the invention is not to be limited by the foregoing implementations, but only by the following claims.

We claim:

1. A method of compensating for a movement of a device worn by a user, the method comprising:
   measuring, using a first sensor of the device, a motion of the head of the user wearing the device;
   measuring, using a second sensor, a motion of the device;
   determining a difference in the motion of the device with respect to the motion of the head of the user; and
   compensating for the difference in the motion of the device with respect to the motion of the head of the user.

2. The method of claim 1 wherein the device comprises at least one of an EEG device, an EOG device, an EKG device, an oxygen detector, a carbon dioxide detector, a chest band, an arm band, or a leg band.

3. The method of claim 1 wherein the device comprises eyewear.

4. The method of claim 3 wherein determining a difference in the motion of the device with respect to the motion of the head of the user comprises measuring a motion of the eyewear using the second sensor on the eyewear and measuring a motion of the user wearing the eyewear using the first sensor.

5. The method of claim 3 wherein compensating for the difference in the motion of the device with respect to the motion of the head of the user comprises cancelling the motion of the head of the user to determine a slip of the eyewear.

6. The method of claim 1 wherein compensating for the difference in the motion of the device with respect to the motion of the head of the user comprises applying an inverse slip transform on an input image, and using a transformed image for pupil-ellipse detection and pupil-point extraction.

7. The method of claim 1 wherein compensating for the difference in the motion of the device with respect to the motion of the head of the user comprises extracting a pupil-point from a pupil-ellipse, and applying an inverse slip transform to the pupil-point.

8. The method of claim 1 wherein compensating for the difference in the motion of the device with respect to the motion of the head of the user comprises applying an inverse slip transform on an input image, and using a transformed image for pupil-ellipse extraction.

9. An electronic monitoring system for monitoring a device worn by a user, the electronic monitoring system comprising:
   a processor coupled to receive data from a first sensor and a second sensor, wherein the processor:
      measures, using the first sensor, a motion of the head of the user wearing the device;
      measures, using the second sensor, a motion of the device;
      determines a difference in the motion of the device with respect to the motion of the head of the user; and
      compensates for the difference in the motion of the device with respect to the motion of the head of the user.

10. The electronic monitoring system of claim 9 wherein the device comprises at least one of an EEG device, an EOG device, an EKG device, an oxygen detector, a carbon dioxide detector, a chest band, an arm band, or a leg band.

11. The electronic monitoring system of claim 9 wherein the device comprises eyewear, and determining a difference in the motion of the device with respect to the motion of the head of the user comprises measuring a motion of the eyewear using the second sensor on the eyewear and measuring a motion of the user wearing the eyewear using the first sensor.

12. The electronic monitoring system of claim 9 wherein the device comprises eyewear, and compensating for the difference in the motion of the device with respect to the motion of the head of the user comprises applying an inverse slip transform on an input image, and using a transformed image for pupil-ellipse detection and pupil-point extraction.

13. The electronic monitoring system of claim 9 wherein the device comprises eyewear, and compensating for the difference in the motion of the device with respect to the motion of the head of the user comprises extracting a pupil-point from a pupil-ellipse, and applying an inverse slip transform to the pupil-point.

14. The electronic monitoring system of claim 9 wherein the device comprises eyewear, and compensating for the difference in the motion of the device with respect to the motion of the head of the user comprises applying an inverse slip transform on an input image, and using a transformed image for pupil-ellipse extraction.

15. A non-transitory computer-readable storage medium having data stored therein representing instructions executable by a processor to perform a method comprising:
   measuring, using a first sensor of a device, a motion of the head of a user wearing the device;
   measuring, using a second sensor, a motion of the device;

determining a difference in the motion of the device with respect to the motion of the head of the user; and compensating for the difference in the motion of the device with respect to the motion of the head of the user.

16. The non-transitory computer-readable storage medium of claim 15 wherein the device comprises at least one of an EEG device, an EOG device, an EKG device, an oxygen detector, a carbon dioxide detector, a chest band, an arm band, or a leg band.

17. The non-transitory computer-readable storage medium of claim 15 wherein the device comprises eyewear, and compensating for the difference in the motion of the device with respect to the motion of the head of the user comprises cancelling the motion of the head of the user to determine a slip of the eyewear.

18. The non-transitory computer-readable storage medium of claim 15 wherein the device comprises eyewear, and compensating for the difference in the motion of the device with respect to the motion of the head of the user comprises applying an inverse slip transform on an input image, and using a transformed image for pupil-ellipse detection and pupil-point extraction.

19. The non-transitory computer-readable storage medium of claim 15 wherein the device comprises eyewear, and compensating for the difference in the motion of the device with respect to the motion of the head of the user comprises extracting a pupil-point from a pupil-ellipse, and applying an inverse slip transform to the pupil-point.

20. The non-transitory computer-readable storage medium of claim 15 wherein the device comprises eyewear, and compensating for the difference in the motion of the device with respect to the motion of the head of the user comprises applying an inverse slip transform on an input image, and using a transformed image for pupil-ellipse extraction.

* * * * *